United States Patent
Jevtic et al.

(10) Patent No.: US 10,337,998 B2
(45) Date of Patent: Jul. 2, 2019

(54) PLASMA GENERATOR ASSEMBLY FOR MASS SPECTROSCOPY

(71) Applicant: Radom Corporation, West Allis, WI (US)

(72) Inventors: Jovan Jevtic, West Allis, WI (US); Ashok Menon, Shorewood, WI (US); Velibor Pikelja, Milwaukee, WI (US)

(73) Assignee: Radom Corporation, West Allis, WI (US)

( * ) Notice: Subject to any disclaimer, the term of this patent is extended or adjusted under 35 U.S.C. 154(b) by 0 days.

(21) Appl. No.: 15/897,663

(22) Filed: Feb. 15, 2018

(65) Prior Publication Data

US 2018/0240661 A1   Aug. 23, 2018

Related U.S. Application Data

(60) Provisional application No. 62/460,382, filed on Feb. 17, 2017.

(51) Int. Cl.

| | |
|---|---|
| *G01N 21/73* | (2006.01) |
| *H01J 37/32* | (2006.01) |
| *G01J 3/02* | (2006.01) |
| *G01J 3/443* | (2006.01) |
| *H01J 37/244* | (2006.01) |
| *H01J 49/04* | (2006.01) |
| *H01J 49/10* | (2006.01) |

(52) U.S. Cl.
CPC ............ *G01N 21/73* (2013.01); *G01J 3/0208* (2013.01); *G01J 3/443* (2013.01); *H01J 37/244* (2013.01); *H01J 37/32201* (2013.01); *H01J 37/32247* (2013.01); *H01J 37/32449* (2013.01); *H01J 49/0404* (2013.01); *H01J 49/105* (2013.01); *G01N 2201/0221* (2013.01)

(58) Field of Classification Search
CPC .. H01J 37/321; H01J 49/105; H01J 37/32192; H01J 37/32229; H01J 37/32247; H01J 37/32532; G01N 22/00; G01N 21/73; H01S 3/0975; H05H 1/30; H05H 1/46; H05H 2001/4652; C23C 16/4586; C23C 16/511; H01L 21/32136; G01J 3/443; G01R 15/16
USPC ...... 250/288, 423 F, 424, 425; 324/633, 713
See application file for complete search history.

(56) References Cited

U.S. PATENT DOCUMENTS

| | | | |
|---|---|---|---|
| 5,698,036 A * | 12/1997 | Ishii | ................ C23C 16/511 118/723 MP |
| 6,265,717 B1 | 7/2001 | Sakata et al. | |
| 2002/0020494 A1* | 2/2002 | Yokogawa | ............ H01J 37/321 156/345.12 |

(Continued)

FOREIGN PATENT DOCUMENTS

| | | |
|---|---|---|
| JP | H06146026 A | 5/1994 |
| JP | 2003273615 | 9/2003 |

(Continued)

*Primary Examiner* — David A Vanore
(74) *Attorney, Agent, or Firm* — Boyle Fredrickson, S.C.

(57) ABSTRACT

A plasma unit for a mass spectroscopy machine generates plasma using a microwave coupled dielectric ring held within a microwave cavity employing part of the mass spectrometer structure to define the microwave cavity, thereby permitting improved proximity of the plasma and plasma ionized sample material to the mass spectrometer aperture.

11 Claims, 2 Drawing Sheets

(56) References Cited

U.S. PATENT DOCUMENTS

| | | | |
|---|---|---|---|
| 2003/0086840 A1 | 5/2003 | Himori et al. | |
| 2003/0160956 A1 | 8/2003 | Chevalier | |
| 2004/0021454 A1* | 2/2004 | Jevtic | G01R 1/06772 324/72.5 |
| 2005/0099133 A1* | 5/2005 | Quon | H01J 37/321 315/111.01 |
| 2006/0137613 A1 | 6/2006 | Kasai | |
| 2006/0283549 A1* | 12/2006 | Aramaki | H01J 37/32091 156/345.28 |
| 2009/0045749 A1 | 2/2009 | Ganachev et al. | |
| 2010/0186672 A1* | 7/2010 | Okuda | C23C 16/4586 118/723 R |
| 2010/0320379 A1 | 12/2010 | Morrisroe | |
| 2011/0000780 A1 | 1/2011 | Tian et al. | |
| 2014/0349068 A1* | 11/2014 | Inglis | C23C 16/01 428/141 |
| 2016/0025656 A1 | 1/2016 | Jevtic et al. | |
| 2016/0029472 A1* | 1/2016 | Jevtic | H05H 1/46 250/288 |
| 2016/0079107 A1* | 3/2016 | Aramaki | H01L 21/6833 156/345.51 |
| 2017/0009376 A1* | 1/2017 | Khan | C23C 16/274 |
| 2017/0011890 A1* | 1/2017 | Aramaki | H01J 37/32532 |
| 2017/0027051 A1 | 1/2017 | Jevtic et al. | |

FOREIGN PATENT DOCUMENTS

| | | |
|---|---|---|
| JP | 2005251546 A | 9/2005 |
| JP | 2006185923 A | 7/2006 |
| JP | 2009272127 A | 11/2009 |
| JP | 2011232106 A | 11/2011 |
| JP | 2012104424 A | 5/2012 |
| WO | 03096769 A1 | 11/2003 |

* cited by examiner

PLASMA GENERATOR ASSEMBLY FOR MASS SPECTROSCOPY

CROSS REFERENCE TO RELATED APPLICATION

This application claims the benefit of U.S. provisional application 62/460,382 filed Feb. 17, 2017, and hereby incorporated by reference.

BACKGROUND OF THE INVENTION

The present invention relates to mass spectrometer machines and in particular to a plasma generator cavity retrofit that may be retrofit to a variety of different mass spectrometry systems.

Mass spectrometry allows atoms and molecules to be analyzed based on measured mass-to-charge ratios. The samples to be analyzed are first ionized at atmospheric pressure and then transported to a high vacuum mass analyzer through a vacuum interface. Commonly used analyzers include time-of-flight, magnetic sector, and quadrupole mass analyzers. In a time-of-flight mass analyzer the ions are accelerated in an electrical field. The amount of acceleration will be proportional to charge and inversely proportional to mass. A mass-to-charge ratio can thus be determined by measuring a time of flight of the ions (time-of-flight mass spectrometry). In a magnetic sector mass analyzer the accelerated ions are deflected in a magnetic field with the amount of deflection measured by a spatially discriminating sensor after the magnetic field. In a quadrupole mass analyzer a combination of DC and radio-frequency voltages is applied to four parallel rods. Only the ions of the correct mass-to-charge ratio satisfy the resonance condition and are able to reach the detector.

One method of ionizing samples for mass spectroscopy uses an inductively coupled plasma, for example, induced in a gas such as nitrogen or argon by a radiofrequency current passing through a conductive coil such as a copper loop surrounding the plasma. The energy of the plasma couples to the samples to ionize them.

U.S. Pat. No. 9,491,841 assigned to the assignee of the present application and hereby incorporated by reference describes an improved plasma generator using a dielectric ring in place of the copper loop. Current is induced in the ring by energy from a microwave source coupled to a radiofrequency cavity surrounding the ring.

The application of a dielectric plasma generator to mass spectroscopy is challenging because the small distance between the plasma being generated and the sampler cone of the spectroscopy machine do not provide sufficient space for the surrounding radiofrequency cavity, associated waveguides and microwave source needed to feed the cavity. In addition, the small distance makes it difficult to provide the provisions for cooling, gas exhaust, and translational adjustment.

SUMMARY OF THE INVENTION

The present invention provides a compact plasma generator suitable for use with standard mass spectroscopy machines that may make use of a microwave source/dielectric ring construction. The radiofrequency cavity needed to couple to the dielectric ring is shortened by eliminating its wall closest to the mass spectroscopy machine and using the conductive surface of the sampler cone to complete the cavity walls. In one embodiment, an electrically neutral (quartz) separator plate is spaced inward from the sampling cone. This separator plate protects the dielectric ring from the hot plasma gases. A 45-degree waveguide may be used to join the cavity to a microwave source, moving the bulk of the microwave source away from the mounting plane of mass spectrometer against which the radiofrequency cavity is placed.

Specifically, the present invention in one embodiment provides a plasma unit for mass spectroscopy machines of a type providing a sampler cone having an aperture for receiving ionized sample material along an introduction axis therethrough. The plasma unit includes a dielectric annular ring having an axis aligned with the introduction axis and a conductive shell defining a microwave cavity about the dielectric annular ring comprised of electrically joined cavity walls including sidewalls passing around the axis, a rear end wall joining a first edge of the sidewalls, and a front end wall joining an opposite end of the sidewalls and completed by the sampler cone. A microwave generator communicates with the microwave cavity through a first aperture in a side wall to excite the dielectric annular ring into resonance to produce an axially extending plasma; and a sample introduction assembly passes through a second aperture in the rear end wall to inject the sample material axially into the dielectric annular ring for ionization.

It is thus a feature of at least one embodiment of the invention to provide a microwave cavity allowing close positioning of a plasma generating dielectric near the aperture of the sampler plate. By employing the sampler plate as part of the cavity, the interfering structure is eliminated and close proximity obtained.

The plasma unit may further include a support plate adapted to attach to the mass spectroscopy machine around the sampler cone, the support plate supporting the dielectric annular ring, conductive shell, microwave generator, and sample introduction assembly.

It is thus a feature of at least one embodiment of the invention to provide a plasma unit that can be adapted for a variety of different mass spectrometers by use of the support plate that can be received by the mass spectrometer's normal mounting surface.

The support plate may surround the sampler cone and may be electrically joined thereto to provide a portion of the front end wall of the microwave cavity.

It is thus a feature of at least one embodiment of the invention to properly size the microwave cavity independent of the sampler cone dimensions while eliminating unnecessary separation between the microwave cavity and the sampler cone.

The support plate may electrically communicate with the sampler cone through a conductive gasket.

It is thus a feature of at least one embodiment of the invention to provide a simple method of insuring electrical continuity between the cavity and the sampler cone allowing the sampler cone to act like a cavity surface. It is another feature of at least one embodiment of the invention to accommodate slight differences in the recessing of the sampler cone among different mass spectrometry machines through the use of a flexible gasket material.

The plasma unit may further include an electrically neutral divider plate spaced from the sampler cone within the microwave cavity and providing a thermal barrier thermally containing heat from the plasma generated in the region between the neutral divider plate and the sampler cone.

It is thus a feature of at least one embodiment of the invention to protect the dielectric material from high-temperature plasma in a contained system through the use of the electrically neutral isolation plate within the cavity, dividing the cavity thermally but not electrically.

The divider plate may include an axially extending collar supporting the sample introduction assembly.

It is thus a feature of at least one embodiment of the invention to provide a simple support structure that properly aligns the sample introduction assembly without interfering with the electrical properties of the microwave cavity.

The sample introduction assembly may include a sample introduction tube receiving the sample material and directing the same toward the aperture in the sampler cone, the sample introduction to be surrounded by a gas sheath tube surrounding the sample material with a gas sheath directed toward the aperture in the sampler cone.

It is thus a feature of at least one embodiment of the invention to permit the introduction of the carrier and/or plasma forming gas.

The support plate may include an exit port providing an exit path of gases from the sample introduction assembly along the surface of the sampler cone.

It is thus a feature of at least one embodiment of the invention to provide a venting of introduced gases adaptable to a wide variety of different mass spectroscopy machines.

The microwave generator may communicate with the microwave cavity through a waveguide directed at an angle from a perpendicular to the axis of the dielectric annular ring, for example, at 45 degrees with respect to the axis of the dielectric annular ring.

It is thus a feature of at least one embodiment of the invention to permit a displacement of any bulk of the microwave generator away from the mounting surfaces to prevent interference with close proximity of the plasma to the sampler cone.

The dielectric annular ring may be suspended within the cavity on an electrical insulator, for example, having a lower dielectric constant than material of the dielectric annular ring.

It is thus a feature of at least one embodiment of the invention to properly position the dielectric ring without interference with its electrical properties The microwave generator and cavity may cooperate to induce a circumferentially flowing current reciprocating about the axis in the dielectric annular ring. In this regard, the microwave cavity may be a cylindrical cavity having a cylinder axis aligned with the axis of the dielectric ring.

It is thus a feature of at least one embodiment of the invention to promote a circumferential current flow determined to provide a robust and stable plasma at high electrical efficiency.

These particular objects and advantages may apply to only some embodiments falling within the claims and thus do not define the scope of the invention.

DETAILED DESCRIPTION OF THE PREFERRED EMBODIMENT

Figure 1:
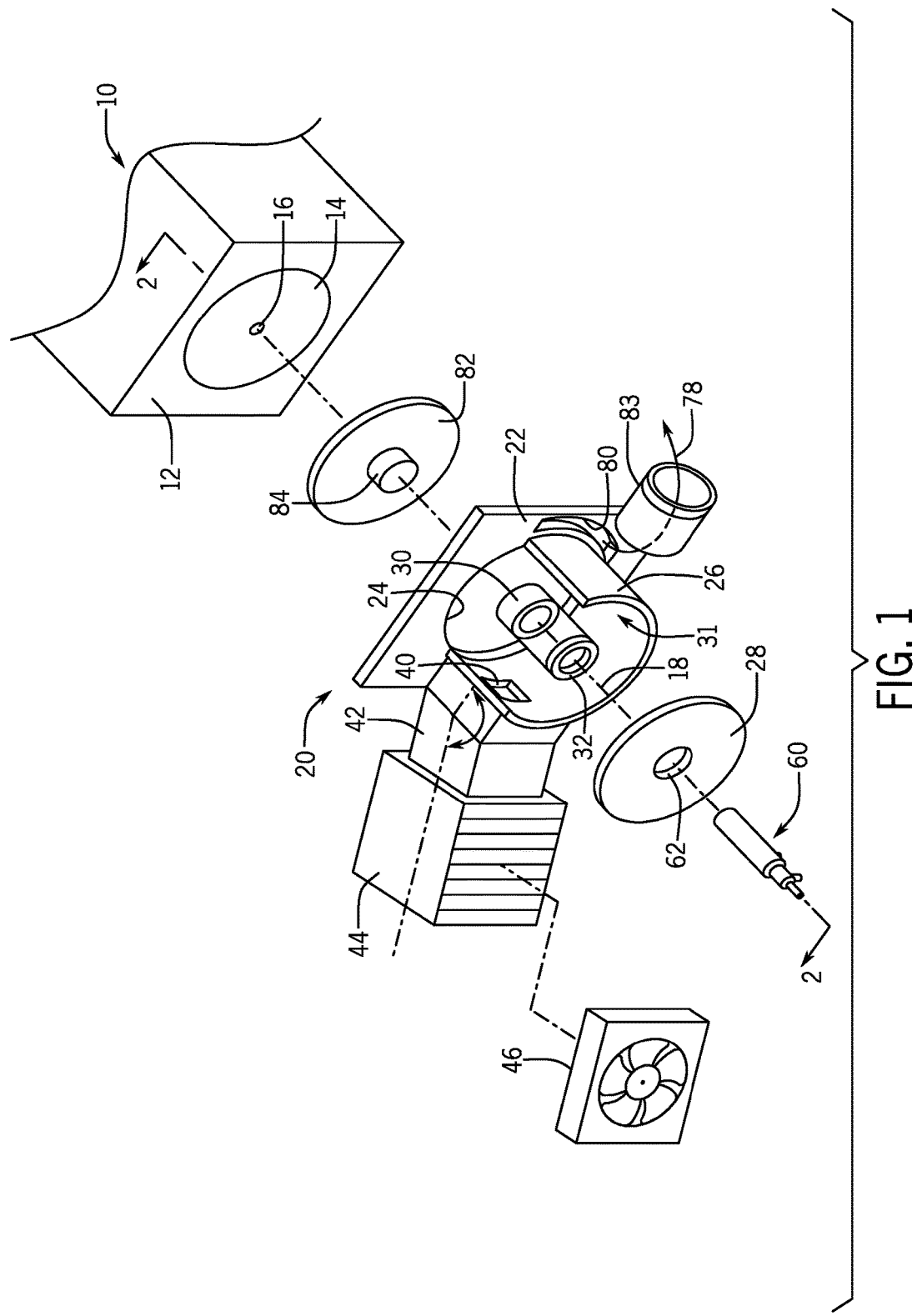
FIG. 1 is an exploded diagram showing the sampling cone of a mass spectrometer at a mounting plane and the plasma cavity assembly of the present invention.
Figure 2:
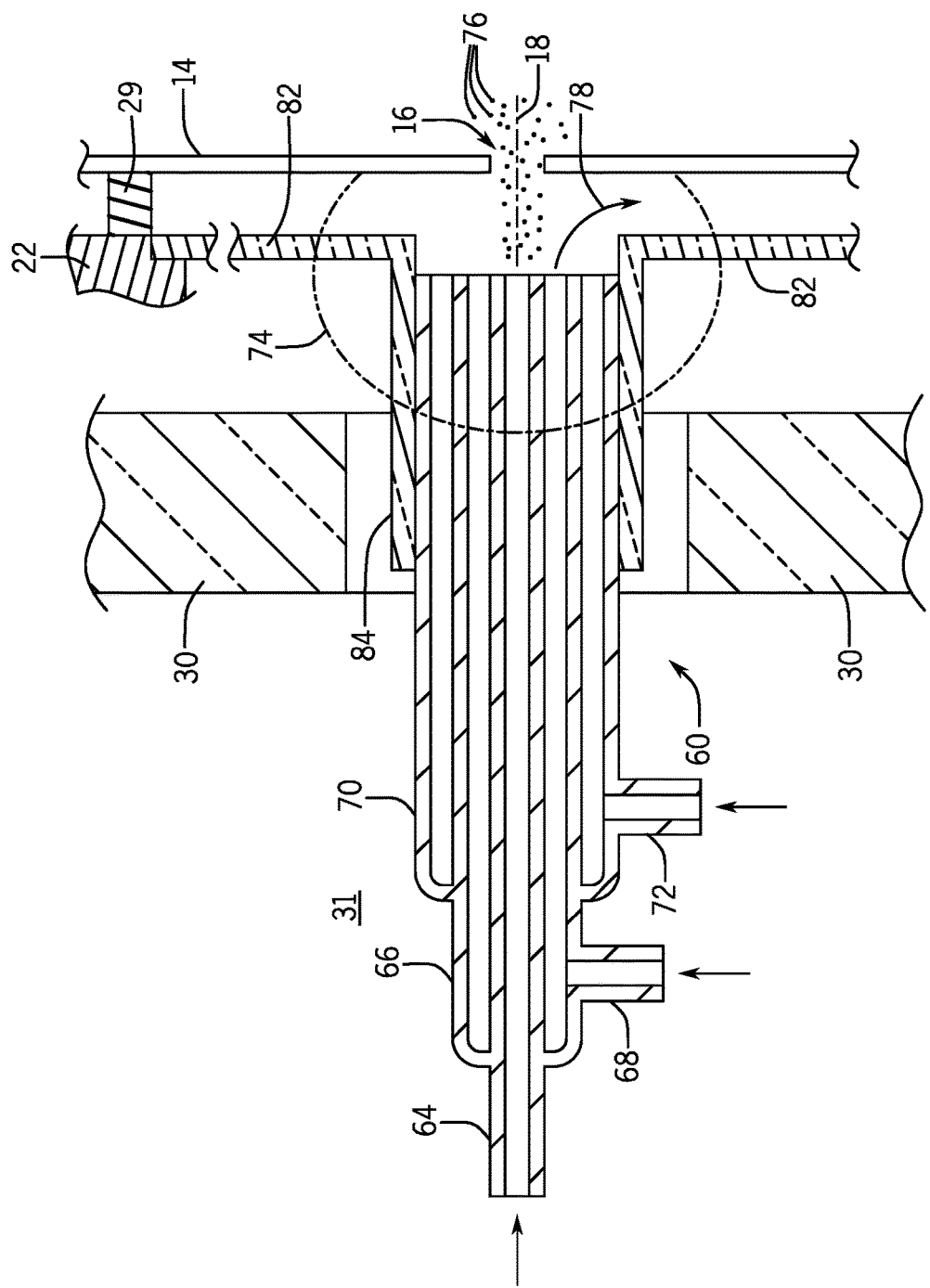
FIG. 2 is a cross-sectional view of the assembled mass spectrometer and plasma cavity taken along line 2-2 of FIG. 1.

Referring now to FIGS. 1 and 2, a mass spectrometer 10 may provide for a mounting surface 12 extending generally along a mounting plane and exposing a sampler cone 14 having a central orifice 16 for receiving an ionized sample for analysis by the mass spectrometer 10. The mounting surface 12 may provide for various clamps or fixtures (not shown) for holding sample-generating apparatus against the mounting surface 12 to provide a stream of ions along an axis 18 for receipt through the central orifice 16.

The sampler cone 14 may be a circular disk of conductive metal such as nickel or platinum resistant to high temperatures.

A plasma source 20 of the present invention may provide a mounting plate 22 attached to abut the mounting surface 12. The mounting plate 22 may be electrically conductive (for example, aluminum) and is held to the mounting surface 12 so as to provide for an electrical connection between the sampler cone 14 and the mounting plate 22 and the conductive structure attached to the mounting plate 22.

The mounting plate 22 provides a circular cutout 24 that is spaced closely to the sampler cone 14 (separated by a few millimeters) so that the sampler cone 14 may form one wall of a cylindrical radiofrequency cavity 31 completed by conductive cylinder 26 (the latter extending rearwardly from the circular cutout 24) and an end plate 28 covering the rear base of the conductive cylinder 26.

In order to provide for translational adjustment in two directions orthogonal to the axis 18, typically plus-minus 5 mm, the conductive cylinder 26 may be provided with flanges with slots such that the bolts securing the conductive cylinder 26 to the mounting plate 22 are allowed to move in the slots before tightening.

The sampler cone 14, conductive cylinder 26, end plate 28 are electrically joined to provide for a resonant radiofrequency cavity 31 with a mode that will produce reciprocating circumferential current flow in a dielectric doughnut 30 centered along axis 18 serving to generate a plasma for ionization material entering the central orifice 16. This electrical joining may be, for example, by means of a conductive gasket 29 (shown in FIG. 2) or through other electrically conductive intervening structures.

The dielectric doughnut 30 may be supported, for example, by a Teflon holder 32 supported by the end plate 28 and may be constructed according to the aforementioned patent incorporated by reference herein.

Microwave energy is introduced into the radiofrequency cavity 31 through an entrance port 40 in an outer circumferential wall of the cavity 31. This entrance port 40 may be adjustable, for example, through the use of an iris or replaceable plates having different sizes of openings. The port 40 leads out of the radiofrequency cavity 31 to a 45 degree bend waveguide 42 having a first portion attached to the entrance port 40 extending parallel to the plane of the mounting surface 12 and a second portion angled at 45 degrees away from the mounting plane of mounting surface 12. As an alternative to using a waveguide bend, a straight waveguide channel, opening directly into the cavity 31, may be bored into the body of the conductive cylinder 26 such that the axis of the waveguide channel and the axis 18 form an angle different than 90 degrees, typically between 60 and 80 degrees. A microwave source 44 such as a magnetron is then attached to the outer and of the waveguide 42 so as to be removed from interference with a structure lying along the mounting plane of surface 12. A cooling fan 46 may be mounted on a side of the microwave source 44 away from the mounting plane of surface 12 to reduce the amount of bend and distance of the waveguide necessary to provide adequate clearance.

A torch assembly 60 may fit through an opening 62 in the end plate 28 to be received through the doughnut 30 aligned with axis 18. As is generally understood in the art, the torch assembly includes a central lumen 64 for the introduction of sample material that will be directed toward the central orifice 16. The central lumen 64 passes inside of two concentric outer sleeves, a first sleeve 66 receiving cooling gas through a cooling gas inlet 68 and a second sleeve 70 outside of the first sleeve 66 receiving cooling gas through cooling gas inlet 72. Generally the cooling gas will be argon or nitrogen so that this gas is discharged through the doughnut 30 into a plasma region 74 to be converted to a neutral plasma which ionizes the sample material 76 for receipt through the central orifice 16.

Referring specifically to FIG. 2, an electrically neutral high temperature divider plate 82 may be supported by the plate 22 between the sampler cone 14 and the dielectric doughnut 30. Desirably the high temperature divider plate may be a perfect insulator with a dielectric constant lower than the dielectric doughnut 30, for example, a quartz material. This divider plate 82 may have a central aperture to which is attached to a rearwardly extending cylindrical collar 84 that may slidably receive the torch assembly 60 for creating a thin (approximately 0.5 mm) and long (approximately 20 mm) annular space between the torch assembly 60 and the cylindrical collar 84 with the purpose of minimizing the reverse flow of hot gas 78 into the interior of the cavity 31.

Excess heated gas from the plasma is drawn as indicated by arrow 78 between the sampler cone 14 and the divider plate 82 and out of an aperture 80 (shown in FIG. 1) in plate 22 to be received by an exhaust duct system 83. In this regard, the divider plate 82 serves to protect the dielectric doughnut 30 from the hot gases 78 without changing the electrical properties of the cavity 31.

By using the sampler cone 14 as a portion of the radiofrequency cavity 31 and providing an electrically neutral divider plate 82 resistant to the high temperature gases, inductive coupling to the doughnut 30 may be obtained in extremely compact arrangement.

Small holes (approximately 5 mm diameter) may be provided on the sides of the cylindrical conductor 26 in order to provide for the flow of cooling air and to allow for the visual monitoring of the plasma conditions.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. A plasma unit for mass spectroscopy machines of a type providing a sampler cone having an aperture for receiving ionized sample material along an introduction axis therethrough, the plasma unit comprising
   a dielectric annular ring having an axis aligned with the introduction axis;
   a conductive shell defining a microwave cavity about the dielectric annular ring comprised of electrically joined cavity walls including sidewalls passing around the axis, a rear end wall joining a first edge of the sidewalls and a front end wall joining an opposite end of the sidewalls and completed by the sampler cone when the plasma unit is installed on the mass spectroscopy machine;
   a microwave generator communicating with the microwave cavity through a first aperture in a side wall to excite the dielectric annular ring into resonance to produce an axially extending plasma; and
   a sample introduction assembly passing through a second aperture in the rear end wall to inject the ionized sample material axially into the dielectric annular ring for ionization;
   further including a support plate adapted to attach to the mass spectroscopy machine around the sampler cone, the support plate supporting the dielectric annular ring, conductive shell, microwave generator and sample introduction assembly.

2. The plasma unit of claim 1 wherein the support plate surrounds the sampler cone and is electrically joined thereto and provides a portion of the front end wall of the microwave cavity.

3. The plasma unit of claim 1 wherein the support plate electrically communicates with the sampler cone through a conductive gasket.

4. A plasma unit for mass spectroscopy machines of a type providing a sampler cone having an aperture for receiving ionized sample material along an introduction axis therethrough, the plasma unit comprising a dielectric annular ring having an axis aligned with the introduction axis;

a conductive shell defining a microwave cavity about the dielectric annular ring comprised of electrically joined cavity walls including sidewalls passing around the axis, a rear end wall joining a first edge of the sidewalls and a front end wall joining an opposite end of the sidewalls and completed by the sample cone when the plasma unit is installed on the mass spectroscopy machine;

a microwave generator communicating with the microwave cavity through a first aperture in a side wall to excite the dielectric annular ring into resonance to produce an axially extending plasma; and a sample introduction assembly passing through a second aperture in the rear end wall to inject the ionized sample material axially into the dielectric annular ring for ionization;

further including electrically neutral divider plate spaced from the sampler cone within the microwave cavity providing a thermal barrier thermally containing heat from the plasma generated in the region between the neutral divider plate and the sampler cone.

5. The plasma unit of claim 4 wherein the divider plate includes an axially extending collar supporting the sample introduction assembly.

6. The plasma unit of claim 5 wherein the sample introduction assembly includes a sample introduction tube receiving the sample material and directing the same toward the aperture in the sampler cone, the sample introduction to be surrounded by a gas sheath tube surrounding the sample material with a gas sheath directed toward the aperture in the sampler cone.

7. The plasma unit of claim 6 wherein the support plate includes an exit port providing an exit path of gases from the sample introduction assembly along the surface of the sampler cone.

8. The plasma unit of claim 4 wherein the resonance provides a circumferentially flowing current reciprocating about the axis in the dielectric annular ring.

9. The plasma unit of claim 4 wherein the microwave cavity is a cylindrical cavity having a cylinder axis aligned with the axis of the dielectric ring.

10. A plasma unit for mass spectroscopy machines of a type providing a sampler cone having an aperture for receiving ionized sample material along an introduction axis therethrough, the plasma unit comprising a dielectric annular ring having an axis aligned with the introduction axis; a conductive shell defining a microwave cavity about the dielectric annular ring comprised of electrically joined cavity walls including sidewalls and a front end wall joining an opposite end of the sidewalls and completed by the sampler cone when the plasma unit is installed on the mass spectrometry machine; a microwave generator communicating with the microwave cavity through a first aperture in a side wall to excite the dielectric annular ring into resonance to produce an axially extending plasma; and a sample introduction assembly passing through a second aperture in the rear end wall to inject the ionized sample material axially into the dielectric annular ring for ionization; wherein the microwave generator communicates with the microwave cavity through a waveguide directed at an angle away from a perpendicular to the introduction axis; wherein the waveguide is directed at at least 45 degrees with respect to the introduction axis.

11. A plasma unit for mass spectroscopy machines of a type providing a sampler cone having an aperture for receiving ionized sample material along an introduction axis therethrough, the plasma unit comprising a dielectric annular ring having a n axis aligned with the introduction axis; a conductive shell defining a microwave cavity about the dielectric annular ring comprised of electrically joined cavity walls including sidewalls and a front end wall joining an opposite end of the sidewalls and completed by the sampler cone when the plasma unit is installed on the mass spectrometry machine; a microwave generator communicating with the microwave cavity through a first aperture in a side wall to excite the dielectric annular ring into resonance to produce an axially extending plasma; and a sample introduction assembly passing through a second aperture in the rear end wall to inject the ionized sample material axially into the dielectric annular ring for ionization; wherein the dielectric annular ring is suspended within the cavity on an electrical insulator; wherein the electrical insulator is a dielectric material having a lower dielectric constant than material of the dielectric annular ring.

* * * * *